United States Patent [19]

Wiles

[11] Patent Number: Plant 5,919

[45] Date of Patent: Mar. 31, 1987

[54] ACHIMENES PLANT NAMED BLUE ROSE

[75] Inventor: Linda S. Wiles, Greenwood, S.C.

[73] Assignee: Geo. W. Park Seed Co., Inc., Greenwood, S.C.

[21] Appl. No.: 722,716

[22] Filed: Apr. 9, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

An Achimenes plant named Blue Rose having double flower form with five full size petals and four-six smaller petals, attractive violet-blue flower color, floriferous flowering habit, and a rapid growth habit.

2 Drawing Figures

The present invention comprises a new and distinct cultivar of Achimenes plant, hereinafter referred to by the cultivar name Blue Rose.

Blue Rose is a product of a planned breeding program which had the objective of creating new Achimenes cultivars having superior vigor, good branching habits, suitability for pot plants or hanging baskets, double flowers 2" or more in diameter and of various colors, early-flowering, floriferousness, and a long flowering season. Such traits in combination were not present or needed improvement in previously available commercial cultivars of this type.

Blue Rose was originated from a hybridization made in a controlled breeding program in Greenwood, S.C. in 1981. Both the male and female parent were identified by the same breeding number 810027-1, with the male parent being selfed from the female parent.

Blue Rose was discovered and selected as one flowering plant within the progeny of the stated parentage by Linda Saussy Wiles on June 21–25, 1982 in a controlled greenhouse environment in Greenwood, S.C.

Asexual reproduction of the new cultivar by rhizomes, as performed initially by Linda Saussy Wiles at Greenwood, S.C. has demonstrated that the combination of characteristics as herein disclosed for Blue Rose are firmly fixed through successive generations of asexual reproduction.

Blue Rose has not been observed under all possible environmental conditions. The phenotype may vary significantly with variations in environment such as temperature, light intensity, and day length. The following observations, measurements and comparisons describe plants grown in Greenwood, S.C. under greenhouse conditions which approximate those generally used in commercial practice.

The following traits have been repeatedly observed and are determined to be basic characteristics of Blue Rose, which in combination distinguish this Achimenes as a new and distinct cultivar:

(1) The flowers are double in form and 1.7" to 2.0" in diameter. There are five (5) full size petals, and four to six or more smaller petals measuring 0.6"×0.6" or more when fully expanded.

(2) The upper surface flower color of the outer petals is an attractive violet-blue, with the petals showing silver-white on the reverse or underside. Under stress conditions, double petals may retract somewhat into the throat showing HCC 601/3 (Primrose Yellow), with some lines and dots of HCC 28 (Fuchsia Purple) also being apparent.

(3) Generally, two to three flowers appear at each internode. Plants are erect when young, and semi-trailing towards end of growing season.

(4) Rhizomes start growing early, producing plants rapidly. From rhizomes planted February 11th, flowering plants were available May 20th.

(5) Plants continue to flower well into late October or early November.

(6) Highly floriferous flowering habit.

The accompanying color photographic drawings show typical inflorescence and foliate characteristics of Blue Rose, with the colors being as nearly true as possible with illustrations of this type.

Sheet 1 is a perspective view of the plant, and

Sheet 2 comprises a greatly enlarged photo of a single flower and surrounding foliage.

In the following description, color references are made to the Horticultural Color Chart (HCC), or to The Royal Horticultural Society Colour Chart (RHS) where indicated. The color values were determined between 11:00 a.m. and 1:00 p.m. on Sept. 18, 1984 under 5000 foot candles of light intensity at Greenwood, S.C.

Classification:

A. *Botanical.*—Achimenes hybrid., cv Blue Rose.

B. *Commercial.*—Achimenes.

I. PLANT

A. General appearance:

*Height.*—Erect when young; semi-trailing later.

*Growth.*—Bushy.

*Internode.*—Distance 0.7"–1.2" (1.8 cm to 3.0 cm.).

B. Foliage:

*Leaves.*—Numerous.

*Shape.*—1.0" by 1.7" to 2.5" (2.5 cm by 4.3 to 6.4 cm).

*Appearance.*—Serrated.

*Color.*—Top side HCC 0962 Parsley Green. Bottom side HCC 06¾ Pod Green.

*Texture.*—Pubescent on both upper and lower surfaces.

C. Flowers:

*Borne.*—2–3 flowers per internode at most internodes.

*Type of stems.*—Short.

*Number of flowers per stem.*—One.

*Quantity of blooms.*—Abundant.

D. Blooms:

*Size.*—1.7 to 2.0" (4.3 cm to 5.0 cm).

*Petalage.*—Double; five (5) full size outer petals, 4–6 or more smaller inner petals.

*Shape.*—Approximately round.

*Color.*—Precise color values are very difficult to obtain in view of the continuous, floriferous flowering habit and the fading of petal color as the flowers mature. Newly opening flowers (upper surface) are HCC 40/1 to HCC 40/2, progressively but non-uniformly fading to HCC 39/1 and H.C.C. 39/2, with all of these colors sometimes appearing. The under surface of the petals are silver-white.

If inner petals retract, a white throat is visible with HCC 601/3 (Primrose Yellow), with 5 lines and many dots of HCC 28 (Fuchsia Purple).

E. Reproductive organs:

*Stamens.*—0–4.

*Filaments.*—Four (4), sometimes attached to petals.

*Anthers.*—Variable, 0–4.

*Pollen.*—Some formed on occasion.

*Pistils.*—One.

*Styles.*—Normal, one.

*Seed.*—Will not normally produce seed.

Disease resistance: No known disease problems.

I claim:

1. A new and distinct cultivar of Achimenes plant named Blue Rose, as illustrated and described, and particularly characterized by its double flower form having five full size petals and four-six smaller petals, attractive violet-blue flower color, floriferous flowering habit, and by its rapid growth habit.

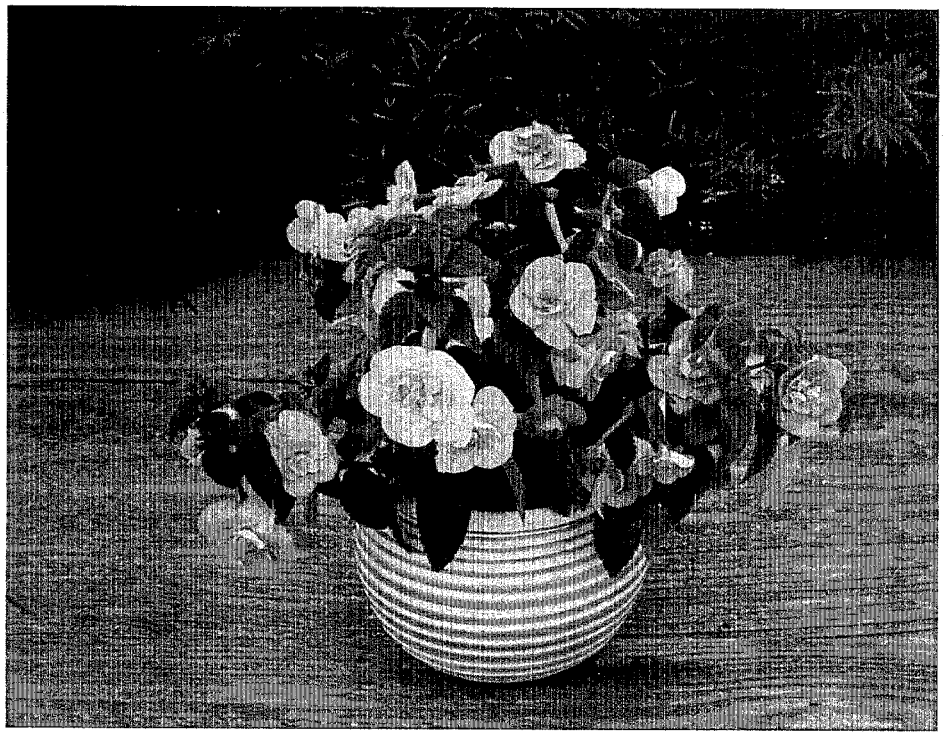

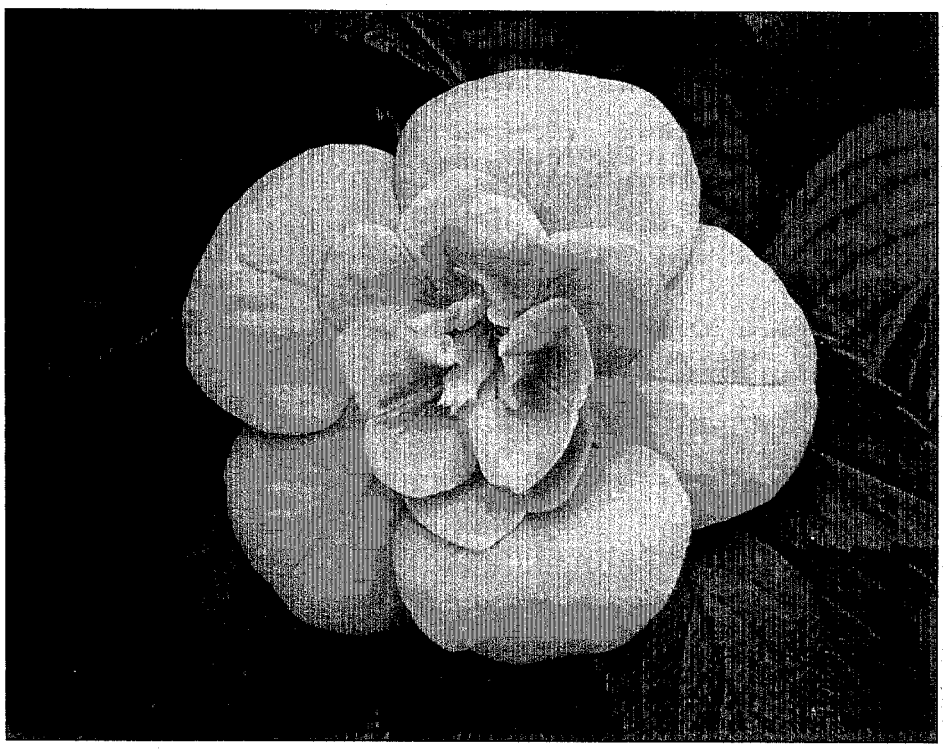

* * * * *